(12) United States Patent
Amidon et al.

(10) Patent No.: US 6,953,672 B2
(45) Date of Patent: Oct. 11, 2005

(54) SCREEN FOR CDC7 INHIBITORS

(75) Inventors: Benjamin Stone Amidon, Arlington, MA (US); Christine Ellen Bulawa, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 145 days.

(21) Appl. No.: 10/225,323

(22) Filed: Aug. 21, 2002

(65) Prior Publication Data

US 2003/0149240 A1 Aug. 7, 2003

Related U.S. Application Data

(60) Provisional application No. 60/313,889, filed on Aug. 21, 2001.

(51) Int. Cl.[7] .............................. C12Q 1/02; C12Q 1/68; C12N 1/14; C12N 1/15; C12N 15/74
(52) U.S. Cl. .......................... 435/29; 435/6; 435/254.1; 435/254.11; 435/255.1; 435/255.7; 435/471
(58) Field of Search ........................... 435/6, 29, 254.1, 435/254.11, 255.1, 255.7, 69.1, 254.2; 440/471; 530/350; 514/12

(56) References Cited

PUBLICATIONS

Jiang, W. et al. "Mammalian Cdc7–Dbf4 protein kinase complex is essential for initiation of DNA replication", 1999, EMBO journal, vol. 18. pp. 5703–5713.*

Johnston, LH et al. "First the CDKs, now the DDKs", 1999, Trends in Cell Biology, vol. 9, p249–252.*

Kim, JM et al. "Growth Regulation of the Expression of Mouse cDNA and Gene Encoding a Serine/Threonine Kinase related to S. Cerevisiae CDC7 Essential for G1/S Transition", 1998, J. Biol. Chem. vol. 273, p. 23248–23257.*

* cited by examiner

*Primary Examiner*—David Guzo
*Assistant Examiner*—Michael D. Burkhart
(74) *Attorney, Agent, or Firm*—Millennium Pharmaceuticals, Inc.

(57) ABSTRACT

Disclosed is a yeast cell whose genetic complement includes an inactive allele of the yeast CDC7 gene, a first nucleic acid that encodes a mammalian Cdc7 protein, and a second nucleic acid that encodes a mammalian Dbf4 protein. The yeast cell is dependent on the mammalian Cdc7 and Dbf4 proteins for viability. The yeast cell can be used to identify potential anti-proliferative agents by virtue of their inhibition of the mammalian Cdc7 and Dbf4 proteins. In some embodiments, a control yeast cell which does not depend on Cdc7 for viability is used in a secondary screen.

9 Claims, 8 Drawing Sheets

```
ATGGAGGCGTCTTTGGGGATTCAGATGGATGAGCCAATGGCTTTTTCTCCCCAGCGTG
ACCGGTTTCAGGCTGAAGGCTCTTTAAAAAAAAACGAGCAGAATTTTAAACTTGCAGG
TGTTAAAAAAGATATTGAGAAGCTTTATGAAGCTGTACCACAGCTTAGTAATGTGTTTA
AGATTGAGGACAAAATTGGAGAAGGCACTTTCAGCTCTGTTTATTTGGCCACAGCACA
GTTACAAGTAGGACCTGAAGAGAAAATTGCTCTAAAACACTTGATTCCAACAAGTCATC
CTATAAGAATTGCAGCTGAACTTCAGTGCCTAACAGTGGCTGGGGGGCAAGATAATGT
CATGGGAGTTAAATACTGCTTTAGGAAGAATGATCATGTAGTTATTGCTATGCCATATC
TGGAGCATGAGTCGTTTTTGGACATTCTGAATTCTCTTTCCTTTCAAGAAGTACGGGA
ATATATGCTTAATCTGTTCAAAGCTTTGAAACGCATTCATCAGTTTGGTATTGTTCACC
GTGATGTTAAGCCCAGCAATTTTTTATATAATAGGCGCCTGAAAAAGTATGCCTTGGTA
GACTTTGGTTTGGCCCAAGGAACCCATGATACGAAAATAGAGCTTCTTAAATTTGTCCA
GTCTGAAGCTCAGCAGGAAAGGTGTTCACAAAACAAATCCCACATAATCACAGGAAACA
AGATTCCACTGAGTGGCCCAGTACCTAAGGAGCTGGATCAGCAGTCCACCACAAAAGC
TTCTGTTAAAAGACCCTACACAAATGCACAAATTCAGATTAAACAAGGAAAAGACGGAA
AGGAGGGATCTGTAGGCCTTTCTGTCCAGCGCTCTGTTTTTGGAGAAAGAAATTTCAA
TATACACAGCTCCATTTCACATGAGAGCCCTGCAGTGAAACTCATGAAGCAGTCAAAGA
CTGTGGATGTACTGTCTAGAAAGTTAGCAACAAAAAAGAAGGCTATTTCTACGAAAGT
TATGAATAGTGCTGTGATGAGGAAAACTGCCAGTTCTTGCCCAGCTAGCCTGACCTGT
GACTGCTATGCAACAGATAAAGTTTGTAGTATTTGCCTTTCAAGGCGTCAGCAGGTTG
CCCCTAGGGCAGGTACACCAGGATTCAGAGCACCAGAGGTCTTGACAAAGTGCCCCAA
TCAAACTACAGCAATTGACATGTGGTCTGCAGGTGTCATATTTCTTTCTTTGCTTAGTG
GACGATATCCATTTTATAAAGCAAGTGATGATTTAACTGCTTTGGCCCAAATTATGACA
ATTAGGGGATCCAGAGAAACTATCCAAGCTGCTAAAACTTTTGGGAAATCAATATTATG
TAGCAAAGAAGTTCCAGCACAAGACTTGAGAAAACTCTGTGAGAGACTCAGGGGTATG
GATTCTAGCACTCCCAAGTTAACAAGTGATATACAAGGGCATGCTTCTCATCAACCAGC
TATTTCAGAGAAGACTGACCATAAAGCTTCTTGCCTCGTTCAAACACCTCCAGGACAAT
ACTCAGGGAATTCATTTAAAAAGGGGGATAGTAATAGCTGTGAGCATTGTTTTGATGA
GTATAATACCAATTTAGAAGGCTGGAATGAGGTACCTGATGAAGCTTATGACCTGCTT
GATAAACTTCTAGATCTAAATCCAGCTTCAAGAATAACAGCAGAAGAAGCTTTGTTGCA
TCCATTTTTTAAAGATATGAGCTTGTGA (SEQ ID NO:18)
```

FIG. 1A

MEASLGIQMDEPMAFSPQRDRFQAEGSLKKNEQNFKLAGVKKDIEKLYEAVPQL
SNVFKIEDKIGEGTFSSVYLATAQLQVGPEEKIALKHLIPTSHPIRIAAELQCLTVA
GGQDNVMGVKYCFRKNDHVVIAMPYLEHESFLDILNSLSFQEVREYMLNLFKA
LKRIHQFGIVHRDVKPSNFLYNRRLKKYALVDFGLAQGTHDTKIELLKFVQSEAQ
QERCSQNKSHIITGNKIPLSGPVPKELDQQSTTKASVKRPYTNAQIQIKQGKDGKE
GSVGLSVQRSVFGERNFNIHSSISHESPAVKLMKQSKTVDVLSRKLATKKKAIST
KVMNSAVMRKTASSCPASLTCDCYATDKVCSICLSRRQQVAPRAGTPGFRAPEV
LTKCPNQTTAIDMWSAGVIFLSLLSGRYPFYKASDDLTALAQIMTIRGSRETIQAA
KTFGKSILCSKEVPAQDLRKLCERLRGMDSSTPKLTSDIQGHASHQPAISEKTDH
KASCLVQTPPGQYSGNSFKKGDSNSCEHCFDEYNTNLEGWNEVPDEAYDLLDK
LLDLNPASRITAEEALLHPFFKDMSL (SEQ ID NO:19)

FIG. 1B

```
ATGAACTCCGGAGCCATGAGGATCCACAGTAAAGGACATTTCCAGGGTGGAATCCAAG
TCAAAAATGAAAAAAACAGACCATCTCTGAAATCTCTGAAAACTGATAACAGGCCAGAA
AAATCCAAATGTAAGCCACTTTGGGGAAAAGTATTTTACCTTGACTTACCTTCTGTCAC
CATATCTGAAAAACTTCAAAAGGACATTAAGGATCTGGGAGGGCGAGTTGAAGAATTT
CTCAGCAAAGATATCAGTTATCTTATTTCAAATAAGAAGGAAGCTAAATTTGCACAAAC
CTTGGGTCGAATTTCTCCTGTACCAAGTCCAGAATCTGCATATACTGCAGAAACCACTT
CACCTCATCCCAGCCATGATGGAAGTTCATTTAAGTCACCAGACACAGTGTGTTTAAGC
AGAGGAAAATTATTAGTTGAAAAAGCTATCAAGGACCATGATTTTATTCCTTCAAATAG
TATATTATCAAATGCCTTGTCATGGGGAGTAAAAATTCTTCATATTGATGACATTAGAT
ACTACATTGAACAAAAGAAAAAAGAGTTGTATTTACTCAAGAAATCAAGTACTTCAGTA
AGAGATGGGGGCAAAAGAGTTGGTAGTGGTGCACAAAAAACAAGAACAGGAAGACTCA
AAAAGCCTTTTGTAAAGGTGGAAGATATGAGCCAACTTTATAGGCCATTTTATCTTCAG
CTGACCAATATGCCTTTTATAAATTATTCTATTCAGAAGCCCTGCAGTCCATTTGATGT
AGACAAGCCATCTAGTATGCAAAAGCAAACTCAGGTTAAACTAAGAATCCAAACAGATG
GCGATAAGTATGGTGGAACCTCAATTCAACTCCAGTTGAAAGAGAAGAAGAAAAAAGG
ATATTGTGAATGTTGCTTGCAGAAATATGAAGATCTAGAAACTCACCTTCTAAGTGAGC
AACACAGAAACTTTGCACAGAGTAACCAGTATCAAGTTGTTGATGATATTGTATCTAAG
TTAGTTTTTGACTTTGTGGAATATGAAAAGGACACACCTAAAAAGAAAAGAATAAAATA
CAGTGTTGGATCCCTTTCTCCTGTTTCTGCAAGTGTCCTGAAAAAGACTGAACAAAAG
GAAAAAGTGGAATTGCAACATATTTCTCAGAAAGATTGCCAGGAAGATGATACAACAG
TGAAGGAGCAGAATTTCCTGTATAAAGAGACCCAGGAAACTGAAAAAAAGCTCCTGTT
TATTTCAGAGCCCATCCCCCACCCTTCAAATGAATTGAGAGGGCTTAATGAGAAAATGA
GTAATAAATGTTCCATGTTAAGTACAGCTGAAGATGACATAAGACAGAATTTTACACAG
CTACCTCTACATAAAAACAAACAGGAATGCATTCTTGACATTTCCGAACACACATTAAG
TGAAAATGACTTAGAAGAACTAAGGGTAGATCACTATAAATGTAACATACAGGCATCTG
TACATGTTTCTGATTTCAGTACAGATAATAGTGGATCTCAACCAAAACAGAAGTCAGAT
ACTGTGCTTTTTCCAGCAAAGGATCTCAAGGAAAAGGACCTTCATTCAATATTTACTCA
TGATTCTGGTCTGATAACAATAAACAGTTCACAAGAGCACCTAACTGTTCAGGCAAAGG
CTCCATTCCATACTCCTCCTGAGGAACCCAATGAATGTGACTTCAAGAATATGGATAGT
TTACCTTCTGGTAAAATACATCGAAAAGTGAAAATAATATTAGGACGAAATAGAAAAGA
AAATCTGGAACCAAATGCTGAATTTGATAAAAGAACTGAATTTATTACACAAGAAGAAA
ACAGAATTTGTAGTTCACCGGTACAGTCTTTACTAGACTTGTTTCAGACTAGTGAAGAG
AAATCAGAATTTTTGGGTTTCACAAGCTACACAGAAAAGAGTGGTATATGCAATGTTTT
AGATATTTGGGAAGAGGAAAATTCAGATAATCTGTTAACAGCGTTTTTCTCGTCCCCTT
CAACTTCTACATTTACTGGCTTTTAG
(SEQ ID NO:20).
```

FIG. 2A

MNSGAMRIHSKGHFQGGIQVKNEKNRPSLKSLKTDNRPEKSKCKPLWGKVFYL
DLPSVTISEKLQKDIKDLGGRVEEFLSKDISYLISNKKEAKFAQTLGRISPVPSPE
SAYTAETTSPHPSHDGSSFKSPDTVCLSRGKLLVEKAIKDHDFIPSNSILSNALS
WGVKILHIDDIRYYIEQKKKELYLLKKSSTSVRDGGKRVGSGAQKTRTGRLKKP
FVKVEDMSQLYRPFYLQLTNMPFINYSIQKPCSPFDVDKPSSMQKQTQVKLRIQ
TDGDKYGGTSIQLQLKEKKKKGYCECCLQKYEDLETHLLSEQHRNFAQSNQYQ
VVDDIVSKLVFDFVEYEKDTPKKKRIKYSVGSLSPVSASVLKKTEQKEKVELQHI
SQKDCQEDDTTVKEQNFLYKETQETEKKLLFISEPIPHPSNELRGLNEKMSNKC
SMLSTAEDDIRQNFTQLPLHKNKQECILDISEHTLSENDLEELRVDHYKCNIQAS
VHVSDFSTDNSGSQPKQKSDTVLFPAKDLKEKDLHSIFTHDSGLITINSSQEHLT
VQAKAPFHTPPEEPNECDFKNMDSLPSGKIHRKVKIILGRNRKENLEPNAEFDK
RTEFITQEENRICSSPVQSLLDLFQTSEEKSEFLGFTSYTEKSGICNVLDIWEEE
NSDNLLTAFFSSPSTSTFTGF (SEQ ID NO:21).

FIG. 2B

−Dox

+Dox (5μg/ml)

1 & 13 still carry
Yeast CDC7

14, 16, 17, & 18
tetO-HsCDC7/HsDBF4

US 6,953,672 B2

SCREEN FOR CDC7 INHIBITORS

CROSS-REFERENCE TO RELATED APPLICATIONS

This application claims priority from U.S. Provisional Patent Application Ser. No. 60/313,889, filed on Aug. 21, 2001, which is incorporated herein by reference in its entirety.

TECHNICAL FIELD

This invention relates to methods for identifying antiproliferative agents for mammalian cells.

BACKGROUND

Neoplastic disorders such as cancer are characterized by unregulated cell proliferation. Cancer cells progress through a cycle of cellular events that include DNA replication and mitosis. A common strategy for treating such a disorder is to administer agents that inhibit either of these two events. Methotrexate, for example, is an exemplary chemotherapeutic agent for treating cancer. Methotrexate blocks DNA replication by inhibiting dihydrofolate reductases, enzymes that are required for the production of the nucleotide substrates for replication.

Eukaryotic DNA replication is a highly conserved process. Eukaryotes from fungi to mammals utilize highly related proteins to duplicate their genetic material. DNA replication can be separated into two phases: initiation and DNA synthesis. During initiation, the origin recognition complex (ORC) binds to specialized DNA sequences termed "origins." ORC can recruit a hexameric complex of MCM (minichromosome maintenance) proteins that may function as a DNA helicase, which can unwind origins. The MCM complex in turn recruits Cdc45 (cell division cycle-45) protein and other downstream components. As a result, DNA polymerase machinery is loaded onto the origin and DNA replication can be initiated.

In normal cells, these initiation events are precisely regulated. One of the regulators is a complex formed of two proteins, Cdc7 and Dbf4. Cdc7 is a serine-threonine kinase that requires the additional subunit Dbf4 for activity. Both Cdc7 and Dbf4 are essential for survival in *Saccharomyces cerevisiae*. The requirement for either or both of these proteins is alleviated by bob1-1, a mutant allele of the gene CDC46/MCM5.

Dbf4 interacts with origin DNA (Dowell et al., *Science*, 265:1243–1246, 1999). The levels of Dbf4 protein fluctuate during the cell cycle to provide temporal regulation of Cdc7 kinase activity.

Cdc7 interacts with Orc2 in addition to Dbf4 and its kinase substrates (Hardy et al., *Mol. Cell. Biol.*, 16:1832–1841, 1996). Human Cdc7.Dbf4 complex phosphorylates Mcm2 (Jiang et al, EMBO J., 18(20):5703–13, Oct. 15, 1999) to provide a modification which may be required for MCM complex recruitment of Cdc45. Other substrates of Cdc7·Dbf4 may include other MCM proteins, and the p 180 primase subunit.

SUMMARY

In both yeast and mammals, Cdc7 activity is required for cell proliferation. The present invention is based, at least in part, on the discovery that a yeast strain that is dependent upon mammalian Cdc7 activity for viability (rather than an endogenous Cdc7 activity) can be used to identify and/or determine whether a test compound is useful as an antiproliferative agent to treat proliferative disorders in mammals. The yeast strain is modified by impairing or deleting an endogenous component of Cdc7 activity, and by including a heterologous component of mammalian Cdc7. If the test compound inhibits mammalian Cdc7, then viability and/or growth of the yeast strain is impaired. Such inhibition is an indication that the test compound is useful for treating proliferative disorders, e.g., cancer.

One exemplary screening method seeks to identify compounds from a library of compounds that reduce the growth of yeast dependent on a heterologous mammalian Cdc7, but does not reduce the growth of yeast whose viability is dependent on the endogenous Cdc7 or is independent of Cdc7. The new methods are adaptable for high-throughput screening.

Accordingly, the invention features a method for determining whether a test compound is an inhibitor of mammalian Cdc7·Dbf4 activity. The method includes: (i) obtaining a yeast cell described herein; (ii) contacting the yeast cell with a test compound; and (iii) assessing growth or cell cycle progression of the yeast cell, wherein a decrease in growth or cell cycle progression indicates that the test compound is an inhibitor of mammalian Cdc7·Dbf4 activity. The genetic complement of the yeast cell includes: a) an inactive allele of the yeast CDC7 gene or the yeast DBF4 gene; b) a first nucleic acid molecule that encodes a mammalian Cdc7 polypeptide; and c) a second nucleic acid molecule that encodes a mammalian Dbf4 polypeptide.

The mammalian Cdc7 polypeptide can be a human Cdc7, and can have the amino acid sequence of SEQ ID NO:19, optionally with at least 1, e.g., 2, 3, 4, 6, 8, 10 or 20, or greater than 20, conservative amino acid substitutions. Cdc7 polypeptides having conservative amino acid substitutions retain one or more of the activities of Cdc7 polypeptides, e.g., serine threonine kinase activity, the ability to associate with Dbf4, the ability to interact with Orc2, and/or the ability (when complexed with Dbf4) to phosphorylate Mcm2. The mammalian Dbf4 polypeptide can be a human Dbf4, and can have the amino acid sequence of SEQ ID NO: 21, optionally with at least 1, e.g., 2, 3, 4, 6, 8, 10, 20, or greater than 20, conservative amino acid substitutions. Dbf4 polypeptides having conservative amino acid substitutions retain one or more of the activities of Dbf4 polypeptides, e.g., to associate with Cdc7 and/or origin DNA, and the ability (when complexed with Cdc7) to phosphorylate Mcm2.

The first nucleic acid molecule can comprise SEQ ID NO:18 or degenerate variants thereof. The second nucleic acid molecule can comprise SEQ ID NO:20, or degenerate variants thereof. Degenerate variants of a nucleic acid sequence exist because of the degeneracy of the amino acid code; thus, those sequences that vary from the sequence represented by SEQ ID NO:18 or SEQ ID NO:20, but which nonetheless encode a Cdc7 or Dbf4 polypeptide, respectively, are included within the invention.

The assessing can include culturing the yeast cell in a container, e.g, a test tube or petri plate. The assessing can include monitoring the size of a colony formed by the yeast cell; determining, e.g., counting the exact number or estimating the approximate number, of yeast cells in a container, measuring the turbidity of the liquid in the container; measuring endogenous ATP levels; or fluorescent-activated cell sorting based on DNA content. The method can also further include assaying in vitro mammalian Cdc7·Dbf4 kinase activity, e.g., determining whether an MCM protein substrate is phosphorylated.

The invention also features a second method for determining whether a test compound is an inhibitor of a mammalian Cdc7·Dbf4 activity. The method includes (i) contacting a test compound to a first yeast cell, the genetic complement of which includes: (a) an inactive allele of the yeast CDC7 gene; (b) a first nucleic acid molecule that encodes a mammalian Cdc7 polypeptide; and (c) a second nucleic acid molecule that encodes a mammalian Dbf4 polypeptide; (ii) contacting the test compound to a second yeast cell, the viability of which is independent of a mammalian Cdc7 or Dbf4; and (iii) assessing growth or cell cycle progression of the first and second yeast cells, wherein a decrease in growth or cell cycle progression in the first yeast cell relative to the second yeast cell indicates that the test compound is an inhibitor of mammalian Cdc7·Dbf4 activity. The second yeast cell can include a mutant allele of CDC46, e.g., the bob1-1 allele. The first and second yeast cells can each include distinct fluorescent markers, e.g., markers that are spectrally distinct, e.g., green fluorescent protein and yellow fluorescent protein. Further, the first and second yeast cells can be related, e.g., isogenic. The Cdc7 polypeptide can be a human Cdc7 polypeptide. Likewise, the Dbf4 polypeptide can be a human Dbf4 polypeptide.

The method can further include: (iii) repeating (i) and (ii) for multiple test compounds; (iv) identifying candidate compounds that are indicated as inhibitors of mammalian Cdc7·Dbf4 activity; (v) identifying, and selecting a lead compound from the candidate compounds, the lead compound being an inhibitor of Cdc7·Dbf4 activity; and (vi) formulating the selected lead compound as an antiproliferative agent.

In another implementation, the method can further include (iii) repeating (i) and (ii) for multiple test compounds; (iv) identifying candidate compounds that are inhibitors of mammalian Cdc7·Dbf4 activity; (v) isolating one or more lead compounds from the candidate compounds; (vi) derivatizing the one or more lead compounds, thereby producing derivatives of the lead compounds; (vii) identifying one or more derivatives that are indicated as inhibitors of mammalian Cdc7·Dbf4 activity; and (viii) formulating one or more derivatives as an anti-proliferative agent.

In another aspect, the invention features a composition that includes an anti-proliferative agent identified by a method described herein and a pharmaceutically acceptable carrier. Further, a subject having a proliferative disorder can be treated using a method that includes administering the composition to the subject in an amount effective to reduce cell proliferation associated with the proliferative disorder.

In another aspect, the invention features a yeast cell, the genetic complement of which includes a) an inactive allele of the yeast CDC7 gene or the yeast DBF4 gene; b) a first nucleic acid molecule that encodes a mammalian Cdc7 polypeptide; and c) a second nucleic acid molecule that encodes a mammalian Dbf4 polypeptide. The yeast cell can be a haploid or diploid. The yeast can be, for example, Saccharomyces cerevisiae or Schizosaccharomyces pombe.

The mammalian Cdc7 or Dbf4 can be, e.g., human, primate, mouse, rat, horse, dog, or cow Cdc7 or Dbf4. The mammalian Cdc7 or Dbf4 can be at least 80, e.g., 85, 90, 95, or 100% identical to human Cdc7 or Dbf4. In one embodiment, the mammalian Cdc7 is human Cdc7, and the mammalian Dbf4 is human Dbf4. The first and second nucleic acid molecules, which encode mammalian Cdc and Dbf4 polypeptides, respectively, can be at least 80, e.g., 85, 90, 95, or 100% identical to nucleic acid sequences that encode human Cdc7 and Dbf4 polypeptides, respectively.

An example of human Cdc7 is SEQ ID NO:19, as shown in FIG. 1B. An example of a nucleic acid sequence that encodes human Cdc7 is SEQ ID NO:18, as shown in FIG. 1A. Human Cdc7 sequences are recited in GenBank Accession #AF015592. An example of human Dbf4 is SEQ ID NO:21, as shown in FIG. 2B. An example of a nucleic acid that encodes human Dbf4 is SEQ ID NO:20, as shown in FIG. 2A. Human Dbf4 sequences are recited in GenBank Accession #AF160876.

In one embodiment, the first nucleic acid includes a nucleic acid encoding the mammalian Cdc7 protein and a heterologous promoter operably linked to the coding nucleic acid. The nucleic acid can be integrated into a yeast chromosome, or on a plasmid. The promoter can be constitutive or inducible. For example, the promoter can be controllable by an exogenous agent, e.g., a steroid hormone or an antibiotic, e.g., tetracycline.

The yeast cell can further include a nucleic acid that encodes a marker protein, e.g., a fluorescent protein. The yeast cell can further include a mutation in a drug transporter gene, e.g., SNQ2 or PDR5. In some embodiments, the yeast cell further includes a genetic alteration that allows viability of the yeast cell independent of impaired endogenous Cdc7 activity and heterologous Cdc7 activity. The genetic alteration can be a genetically altered allele of CDC46. For example, it can be the P83L allele.

In another aspect, the invention features a nucleic acid that includes: a) a sequence encoding a mammalian Cdc7 or Dbf4 polypeptide; b) a promoter functional in a yeast cell and operably linked to the sequence; and c) a marker sequence that is selectable in a yeast cell. The promoter can include one or more TetR binding sites. The marker sequence can be an auxotrophic marker, e.g., URA3, HIS3, TRP1, LEU2, ADE2, or ADE3. The marker sequence can also confer resistance to an exogenous agent, e.g., kanamycin.

The invention also features a kit that includes: (1) a first yeast cell, the genetic complement of which includes a) an inactive allele of the yeast CDC7 gene or the yeast DBF4 gene, b) a first nucleic acid that encodes a mammalian Cdc7 polypeptide, and c) a second nucleic acid that encodes a mammalian Dbf4 polypeptide; and (2) a second yeast cell, the genetic complement of which includes a) an inactive allele of the yeast CDC7 gene or the yeast DBF4 gene, and b) a mutant allele, which bypasses the requirement for Cdc7·Dbf4 activity. The mammalian Cdc7 or Dbf4 polypeptides can be human Cdc7 or Dbf4 polypeptides, respectively.

As used herein, "Cdc7·Dbf4" refers to the complex of Cdc7 kinase and its associated accessory factor Dbf4. An activity of Cdc7·Dbf4 can include kinase activity directed towards its specific substrates, or any other interaction in which the complex participates to regulate DNA replication.

A "yeast strain," as used herein, refers to a population of fungal cells that each have substantially the same genome content. Thus, the definition encompasses a population of cells that has a subpopulation that includes a plasmid, which may be lost at some frequency—provided that the plasmid is not specifically required as detailed herein. The definition also encompasses a population of yeast cells having minor variations such as loss or movement of a transposon; incidental random mutation; and epigenetic variation. The term "yeast cell" can encompass a population originating from an original cell when appropriate, e.g., when a method requires looking at more than one cell such as when measuring turbidity.

A "lead compound" is a test compound that impairs the growth or viability of a yeast strain that depends on a mammalian Cdc7 activity. If desired, lead compounds can subsequently be derivatized using conventional medicinal chemistry methods, as described herein.

As used herein, the term "subject" is used throughout the specification to describe an animal, human or non-human, to whom treatment according to the methods of the present invention is provided. Veterinary applications are included within the present invention. The term includes but is not limited to mammals, e.g., humans, other primates, pigs, rodents such as mice and rats, rabbits, guinea pigs, hamsters, cows, horses, cats, dogs, sheep and goats. The term "treatment" is used herein to describe delaying the onset of, inhibiting, or alleviating the effect of a condition, e.g., a proliferative disorder, e.g., cancer.

As used herein, the term "operably linked" means that a nucleic acid sequence is connected to a promoter sequence in a manner that allows for transcriptional expression of the nucleotide sequence in vivo.

A "conservative amino acid substitution" is one in which an amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "cancer," "hyperproliferative," and "neoplastic" are used to describe cells having an abnormal state or condition characterized by rapidly proliferating cell growth. The terms include all types of cancerous growths and oncogenic processes, metastatic tissues and malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences is accomplished using a mathematical algorithm. The percent identity between two amino acid sequences is determined using the Needleman and Wunsch (*J. Mol. Biol.*, 48:444–453 (1970)) algorithm, which has been incorporated into the GAP program in the GCG software package (available on the internet at gcg.com), using either a Blossum 62 matrix or a PAM250 matrix, and a gap weight of 4 and a length weight of 6.

The present invention offers several advantages. For example, various embodiments of the invention can readily be used for high-throughput screening (HTS) of a wide variety of test compounds. Thus, lead compounds can be selected from a large number of test compounds. The assays described herein provide a high level of sensitivity and are expected to detect a range of possible inhibitors of mammalian Cdc7·Dbf4. Such inhibitors can be subsequently modified using standard medicinal chemistry techniques and by evaluating structure-activity relationship (SAR) data. Because the assays are cell-based, they can be used to identify anti-proliferative agents that can efficiently enter eukaryotic cells. Thus, the assays enable the identification of potent anti-proliferative compounds and compounds of structural interest that may have relatively modest potency, but have favorable cell permeability properties.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following description of the preferred embodiments thereof, and from the claims.

BRIEF DESCRIPTION OF THE DRAWINGS

FIGS. 1A–B are representations of the nucleic acid (SEQ ID NO:18) and polypeptide (SEQ ID NO:19) sequences of human Cdc7.

FIGS. 2A–B are representations of the nucleic acid (SEQ ID NO:20) and polypeptide (SEQ ID NO:21) sequences of human Dbf4.

DETAILED DESCRIPTION

The invention provides methods for determining whether a test compound is an inhibitor of mammalian Cdc7·Dbf4, and methods for identifying such inhibitors. A genetically-altered yeast strain that depends on mammalian Cdc7·Dbf4 is used as a primary screen for such compounds. Compounds that reduce the growth rate of this specialized yeast strain are subjected to secondary screens to eliminate compounds that reduce the growth rate by means other than an inhibition of mammalian Cdc7·Dbf4. The remaining compounds are identified as candidate compounds. The candidate compounds can be subjected to in vitro and in vivo assays for efficacy as inhibitors of mammalian Cdc7·Dbf4 and as anti-proliferative agents.

Primary Screen

Figure 3:
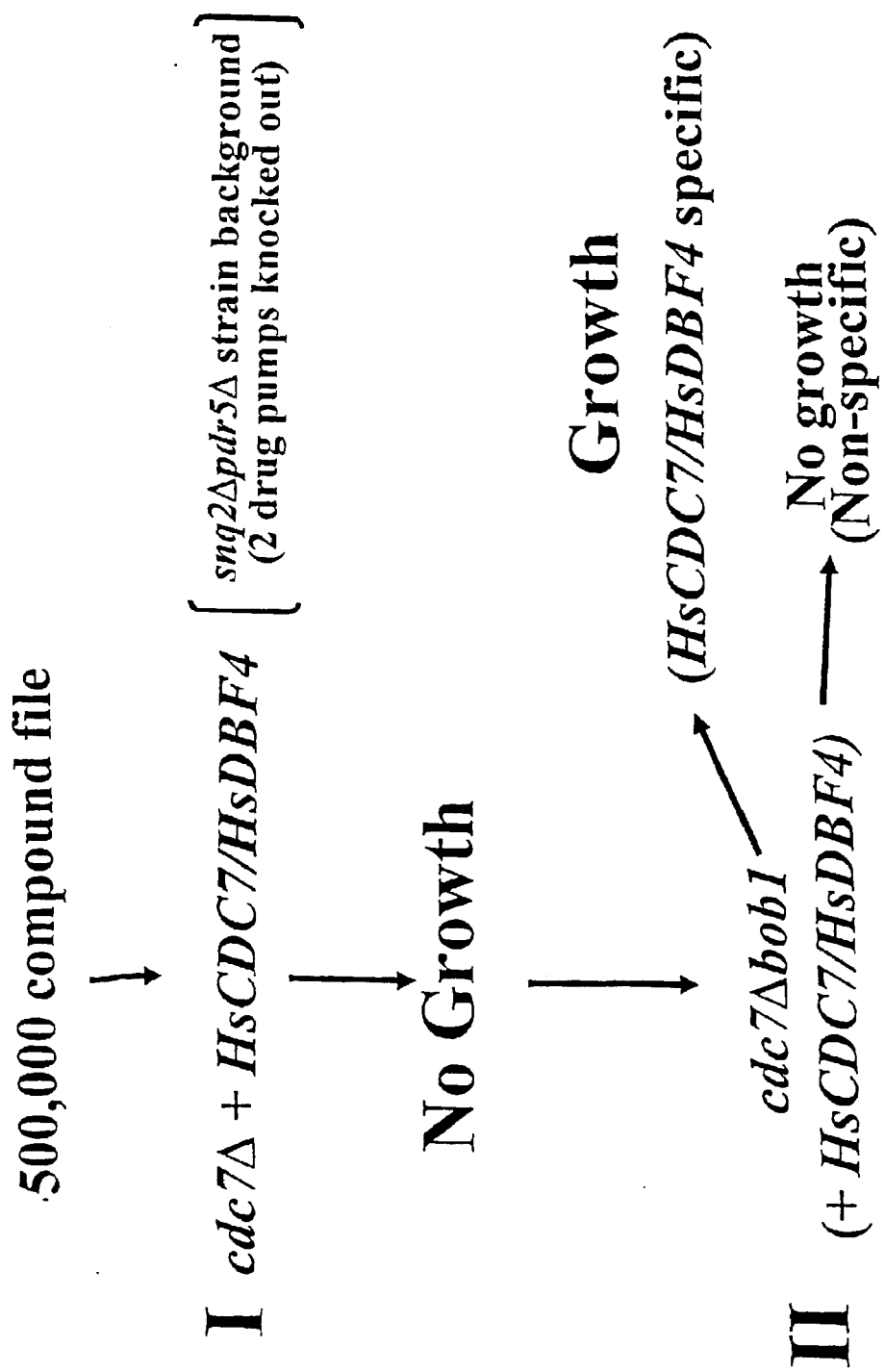
FIG. 3 is a flow chart of an exemplary screening method.

A yeast strain whose viability depends on mammalian Cdc7·Dbf4 is constructed, e.g., as described in Example 1 or as referred to as "Strain 1" (FIG. 3). Typically, human Cdc7 (HsCdc7) and human Dbf4 (HsDbf4) are used. Nucleic acids encoding these polypeptides can be amplified from mammalian, e.g., human, genomic DNA. A wild-type diploid S. cerevisiae strain can be transformed with a DNA cassette that disrupts one copy of the S. cerevisiae CDC7 gene. The resulting heterozygous CDC7$^{+/-}$ strain is transformed with a rescuing plasmid, e.g., a plasmid that expresses yeast CDC7. The transformed heterozygote is sporulated. Haploid spores that have the chromosomal cdc7Δ and the rescuing plasmid are identified. Plasmid shuffle techniques can then be used to replace the rescuing plasmid with one or two constructs that include nucleic acids encoding HsCdc7 and HsDbf4. The resulting yeast strain is dependent on human Cdc7·Dbf4 activity (see below and FIG. 4 and FIG. 5).

The yeast strain dependent on HsCdc7 and HsDbf4 can be used in a variety of growth assays. For example, the strain can be grown in liquid culture in a container such as a test tube, flask or well of a microtitre plate. The container also includes the test compound. The turbidity of the container can be compared with a control container after a suitable incubation time. Alternatively, the cells can be fixed and analyzed for DNA content, e.g., by fluorescence-activated cell sorting. In a further alternative, the abundance of a marker protein such as green fluorescent protein (GFP) or an endogenous protein in the yeast can be assayed. Generally, the determination of growth versus inhibition of growth can be determined by a number of conventional methods including, but not limited to, optical density, reporter gene assays, and determination of endogenous ATP concentration.

In another example, the strain is used to create lawns on petri plates. Filters containing the test compound are placed on the plates. Halos forming in the lawn around the filters, which indicate decreased and/or inhibited growth, can be identified and measured.

The primary screen can identify at least two types of compounds that inhibit the growth of the yeast strain that is dependent on HsCdc7 and HsDbf4 activity. One type of compound includes compounds that are candidate inhibitors of human Cdc7·Dbf4 activity, and hence cell proliferation. These compounds can be formulated as pharmaceutical compositions to treat one or more proliferative disorders, e.g., cancer. The second type of compound includes compounds that are not candidates, but which impair growth of the yeast strain for other reasons. Such compounds may be anti-fungal compounds or compounds that interfere with the heterologous expression system. These compounds can be distinguished from the candidate inhibitors of human Cdc7·Dbf4 activity using the following secondary screens.

Secondary Screens

In one exemplary secondary screen, the growth and/or proliferative activity of a yeast strain that does not depend on any Cdc7 activity is assayed in the presence of the test compound (FIG. 3). This control yeast strain can be similar or identical (i.e., isogenic) to the strain used in the primary screen but includes a bob1-1 mutant allele that bypasses the requirement for Cdc7·Dbf4 activity (regardless of the species origin of Cdc7 or Dbf4).

A secondary screen can be performed concurrently with the primary screen. The strain that depends on HsCdc7 and HsDbf4 and the control yeast strain can be assayed together in the presence of a test compound. The two strains are differentially tagged with different fluorescent proteins (e.g., GFP and derivatives of GFP, e.g., with altered or enhanced fluorescent properties (Clontech Laboratories, Inc. CA), such as yellow fluorescent protein (YFP)). Fluorescent protein expression can be detected by monitoring fluorescence emission upon excitation. The wavelengths are selected depending on the fluorescent properties of the utilized protein. The ratio in fluorescence of the two marker proteins can be compared for the mixture grown in the presence of a test compound relative to a control compound. This method can be done in suspension (e.g., in a test tube or microtiter well), or on a solid or semi-solid surface such as agarose or agar. The method can include x-y translating the microtitre well or medium across a scanning device. Fluorescent ratios for each relevant x-y position can be stored. The system can also store references to compounds applied to each position, and growth data for the screening strain and the control strain.

Test compounds that are not invalidated by one of the secondary screens are candidate inhibitors of human Cdc7·Dbf4 activity. An inhibitor of human Cdc7·Dbf4 activity may function by one of the following exemplary mechanisms: (1) direct inhibition of kinase complex activity; (2) inhibition of substrate recognition; (3) inhibition of the interaction between HsCdc7 and HsDbf4; (4) inhibition of kinase activation; and (5) inhibition of recruitment of HsDbf4 (and complex) to origin of DNA replication. An inhibitor of one or more of these activities can be used to prevent mammalian cell proliferation in vivo or in vitro.

In Vitro Assays

Candidate test compounds can be screened in vitro by assaying the kinase activity of purified HsCdc7 (i.e., human Cdc7 or SEQ ID NO:19) and HsDbf4 (i.e., human Dbf4 or SEQ ID NO:21), e.g., as described in Masai et al. *J. Biol. Chem.* 275:29042–52 (2000). The nucleic acid sequence encoding the two proteins can be cloned into baculovirus expression vectors. One of the two constructs can include a translational fusion of the coding sequence of HsCdc7 or HsDbf4 to a purification tag, e.g., glutathione-S-transferase or hexa-histidine. The two constructs can be co-infected into Sf9 cells to express the proteins. The tagged HsCdc7·HsDbf4 protein complex is then purified using an affinity column. Optionally, additional chromatographic steps can be used to purify the complex.

Similarly, tagging and baculovirus expression systems can be used to purify substrates, such as human Mcm2 or a complex of any two or more of human Mcm2, Mcm4, Mcm6, and Mcm7. In addition, substrates such as *S. cerevisiae* Mcm2 or a complex of any two or more of *S. cerevisiae* Mcm2, Mcm4, Mcm6, and Mcm7 can be overexpressed and purified from *S. cerevisiae*.

To assay a test compound, reaction mixtures are set up with various concentrations of the candidate compound and appropriate controls. The standard reaction mixtures can include 40 mM Hepes.KOH (pH 7.6), 0.5 mM EDTA, 0.5 mM EGTA, 1 mM β-glycerophosphate, 1 mM NaF, 2 mM dithiothreitol, 10 mM magnesium acetate, 80 $\mu$g/ml bovine serum albumin, 0.1 mM ATP, 1 $\mu$Ci of [$\gamma$-$^{32}$P]ATP, 0.1–0.5 $\mu$g of MCM2 (or MCM2-4-6-7 complex) and 50 ng of human HsCdc7.HsDbf4 kinase complex ($\mu$g of protein are per 25 $\mu$l of volume). The reaction is initiated by the addition of either the cold and labeled ATP or the HsCdc7-HsDbf4 complex. The reaction can be incubated, e.g., at 30° C. for 30 minutes. The reaction can be stopped by heat inactivation or the addition of an SDS-PAGE sample buffer. Phosphorylation of the substrate can be measured by immunoprecipitating the substrate onto beads or by separation of the substrate, e.g., on an SDS-PAGE gel.

Test Compounds

The invention provides a method for screening a test compound useful in the prevention or treatment of tumor metastasis. A "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of small molecules include peptides, peptidomimetics (e.g., peptoids), amino acids, amino acid analogs, polynucleotides, polynucleotide analogs, nucleotides, nucleotide analogs, and small molecules, such as organic or inorganic compounds, e.g., heteroorganic or organometallic compounds.

The test compound or compounds can be screened individually or in parallel. An example of the parallel screening is a high throughput drug screen of large libraries of chemicals. Such libraries of test compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

Examples of methods for the synthesis of molecular libraries can be found in the literature, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

Regardless of the method used for screening, compounds that alter the growth or proliferative capacity of a yeast strain dependent on human Cdc7·Dbf4 are considered candidate anti-proliferative compounds. Candidate anti-proliferative compounds can be retested on cancer cells, e.g., in vitro, or tested on animals, e.g., animals that are models for cancer. Candidate compounds that are positive in a retest are considered to be anti-proliforative agents, and can also be used as "lead" compounds to be further optimized and derivatized. A lead compound can be a compound that impairs the growth or viability of a yeast strain that depends on a mammalian Cdc7 activity such that the ratio of A to B is at least 1.2, e.g., 1.5, 2.0, 3.0, or 5.0, where A is the percentage increase in the doubling time of the yeast strain in the presence of the lead compound relative to the same strain in the absence of the compound, and B is the percentage increase in doubling time of a control strain that does not depend on a mammalian Cdc7 activity relative to the same control strain in the absence of the compound.

Once a lead compound has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a lead compound and measure the effects of the modification on the efficacy of the compound to thereby produce derivatives with increased potency. For an example, see Nagarajan et al. (1988) *J. Antibiot.* 41: 1430–8. Furthermore, if the biochemical target of the lead compound is known or determined, the structure of the target and the lead compound can inform the design and optimization of derivatives. Molecular modeling software is commercially available (e.g., Molecular Simulations, Inc.) for this purpose.

Use of Human Cdc7·Dbf4 Inhibitors

A compound identified as a human Cdc7·Dbf4 inhibitor can be used as an anti-proliferative agent to inhibit cell proliferation and/or division of a mammalian cell, e.g., a human cell. Because human Cdc7·Dbf4 activity is required to initiate DNA replication in human cells, inhibition of its activity would prevent cells from advancing through the cell cycle, thereby inhibiting cell proliferation and division.

Examples of cellular proliferative and/or differentiative disorders include cancer, e.g., carcinoma, sarcoma, or metastatic disorders. Specific examples of such disorders include: a fibrosarcoma, myosarcoma, endotheliosarcoma, gastric cancer, esophageal cancer, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, medulloblastoma, craniopharyngioma, melanoma, neuroblastoma, retinoblastoma, leukemia, lymphoma, or Kaposi sarcoma.

Formulation

A composition containing an effective amount of a human Cdc7·Dbf4 inhibitor can be administered (e.g., topically, orally, nasally, buccally, subcutaneously, or intraperitoneally) to an organism in a method of treatment. Treatment typically includes administering an effective amount of the composition to a subject in need of such treatment, thereby inhibiting cell proliferation in the subject. Such a composition typically contains from about 0.1 to 90% by weight (e.g., 1 to 20% or 1 to 10%) of the anti-proliferative agent of the invention in a pharmaceutically acceptable carrier.

Solid formulations of the compositions for oral administration may contain suitable carriers or excipients such gelatin, lactose, acacia, sucrose, kaolin, mannitol, dicalcium phosphate, calcium carbonate, sodium chloride, or alginic acid. Disintegrators that can be used include, without limitation, micro-crystalline cellulose, corn starch, sodium starch glycolate and alginic acid. Tablet binders that may be used include acacia, methylcellulose, sodium carboxymethylcellulose, polyvinylpyrrolidone (Povidone™), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol and polyols (glycerol, propylene glycol, liquid polyethylene glycol, and the like). For intravenous injections, water soluble versions of the compounds may be administered by the drip method, wherein a composition containing the compound and a physiologically acceptable excipient is infused into a subject. Physiologically acceptable excipients may include, for example, 5% dextrose, 0.9% saline, Ringer's solution or other suitable excipients. For intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 0.1 to 20% wt/vol (e.g., 0.1 to 2% wt/vol of essentially pure material) in a carrier such as a pharmaceutical cream base. Various formulations for topical use include drops, tinctures, lotions, creams, solutions, and ointments containing the active ingredient and various supports and vehicles.

Dosage Determination

An appropriate dosage for treatment is determined using standard techniques. For the purposes of inhibiting cell proliferation in a subject, an effective amount of an inhibitor is the amount or dose which is required to ameliorate a neoplasia symptom in a subject. Determination of the amount or dose required to treat an individual subject is routine to one skilled in the art, e.g., a physician, pharmacist, or researcher. First, the toxicity and therapeutic efficacy of the compound is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, e.g., using means to deliver the compound to the affected tissue, i.e., tumor site or proliferative site (e.g., bone marrow).

In formulating a dosage range for use in humans, the effective dose of an inhibitor can be estimated from studies with an animal model for a proliferative disorder. For example, therapeutically effective dosages in cell culture assays are about 5 ng/ml, 50 ng/ml, 500 ng/ml, 5 μg/ml, and 50 μg/ml of inhibitor. A dose can be formulated in an animal to achieve a circulating plasma concentration of inhibitor that falls in this range. An exemplary dose produces a plasma concentration which exceeds the $IC_{50}$ (i.e., the concentration of the test compound which achieves a half-maximal inhibition of a symptom) as determined in cell culture assays. The circulating plasma concentration can be determined, for example, by obtaining a blood sample, and by analyzing the sample with high performance liquid chromatography or mass spectroscopy.

Alternatively, the dose can be estimated from tests in an animal model, e.g., a mouse or primate model for a proliferative disorder. If, for example, the model is a nude mouse have xenografted human tumor cells and an alleviation of symptoms is observed when mice receive a compound in their drinking water at doses of about 4 μg/day, 10 μg/day, 20 μg/day, 40 μg/day, 60 μg/day, and 80 μg/day, then an appropriate dose for treating human patients can be approximately 0.4 mg $kg^{-1}$ $day^{-1}$, 1 mg $kg^{-1}$ $day^{-1}$, 2 mg $kg^{-1}$ $day^{-1}$, 4 mg $kg^{-1}$ $day^{-1}$, 6 mg $kg^{-1}$ $day^{-1}$, or approximately 8 mg $kg^{-1}$ $day^{-1}$. Depending on the method of administration, the appropriate dose can vary, e.g., from about 100 μg $kg^{-1}$ $day^{-1}$ to about 500 mg $kg^{-1}$ $day^{-1}$, 1 mg $kg^{-1}$ $day^{-1}$ to about 100 mg $kg^{-1}$ $day^{-1}$, or 5 mg $kg^{-1}$ $day^{-1}$ to about 50 mg $kg^{-1}$ $day^{-1}$. The dose for a patient can be optimized while the patient is under care of a physician, pharmacist, or researcher. For example, a relatively low dose of the anti-proliferative agent can be administered initially. The patient can be monitored for symptoms of neoplastic activity as described below. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

The efficacy of a dose of an anti-proliferative agent or any other treatment can be determined in a subject. For example, the subject can be monitored for clinical symptoms. Subjects can also be directly monitored for changes in neoplastic activity, e.g., tumor growth and/or metastasis can be monitored, for example, by labeling and imaging techniques, surgery, or physical examination. For example, blood or tissue samples can be obtained from the subject during treatment, and the level of antigens or cells associated with neoplasia can be monitored. Alternatively, histopathologic analysis of samples can be used to determine the efficacy of the agent.

Without further elaboration, one skilled in the art can, based on the above disclosure and the examples discussed below, utilize the present invention to its fullest extent. The following examples are to be construed as merely illustrative of how one skilled in the art can produce and use a yeast strain to identify an anti-proliferative agent, and does not limit of the remainder of the disclosure.

EXAMPLES

Example 1

Construction of a Yeast Strain Dependent on Human CDC7 and DBF4

MMB2334, an example of Strain 1, has the following genotype: cdc7Δ::KAN snq2Δ::HIS3 pdr5Δ::HIS3+p411-tetO:HsCDC7+p415-tetO:HsDSBF4. A yeast cdc7Δ strain that expresses the HsCDC7 and HsDBF4 was constructed as follows.

Creating cdc7Δ::KAN Deletion Strain

The entire open reading frame of CDC7 was deleted using PCR-mediated gene deletion by the method of Wach, et al. ((1994) *Yeast* 10: 1793–1808). Primers oBA234 and oBA235 were used to generate a 1.6 kb PCR product that was transformed into MMB1489 using conventional methods (Sherman, et al. (1979) *Methods in Yeast Genetics*). The following conditions were used for all PCR reactions unless otherwise specified: 94° C. 2 minutes; 25 cycles of 94° C. 30 seconds, 50° C. seconds, 72° C. 4 minutes; then a final incubation at 72° C. for 10 minutes. Amplification of correctly sized products was confirmed by visualizing resolved agarose gels stained with ethidium bromide.

Transformants were selected on rich media supplemented with 200 μg/ml G418 antibiotic. The complete deletion of the CDC7 open reading frame was confirmed by PCR using oBA235 and oBA236 (primer 500 bp upstream of START). This strain was transformed with pRS416-CDC7 (described below), then sporulated and tetrads dissected to obtain a haploid cdc7Δ::KAN carrying pRS416-CDC7.

Cloning of *S. cerevisiae* CDC7

A 2.2 kb fragment containing the entire CDC7 gene was amplified from *S. cerevisiae* genomic DNA by PCR using primers oBA263 and oBA264 and subdloned into the KpnI-EcoRI sites of pRS416. This plasmid is used to generate pRS416-CDC7, and cover a genomic deletion of the yeast CDC7 gene.

Construction of Plasmids p411-tetO and p415-tetO

The entire tetracycline repressible promoter cassette was subcloned from pCM188 into the PvuII sites of pRS411 and pRS416 to generate p411-tetO and p415-tetO, respectively. These plasmids were constructed to permit tetracycline repressible heterologous expression of coding nucleic acids in *S. cerevisiae* with a prototrophic marker other than that in pCM188.

Cloning of Human CDC7 (HsCdc7)

The HsCDC7 mRNA sequence (recited in GenBank Accession #AF015592) encodes the HsCdc7 protein. The complete HsCDC7 open reading frame (ORF) (GenBank Accession #AF015592) was amplified by PCR and subdloned into the NotI site of p411-tetO. The orientation of the subcloned DNA fragment was confirmed by restriction digests and the nucleotide sequence verified by sequence analysis. The cloned ORF is used in a plasmid to introduce HsCdc7 into yeast cells.

Cloning of Human DBF4 (HsDbf4)

The HsDBF4 mRNA sequence is available at GenBank (Accession #AF160876). The entire HsDBF4 ORF was amplified by PCR and subcloned into the NotI site of p415-tetO. The orientation of the subcloned DNA fragment was confirmed by restriction digests and the nucleotide sequence verified by sequence analysis. The cloned ORF is used in a plasmid to introduce HsDbf4 into yeast cells.

Figure 4:
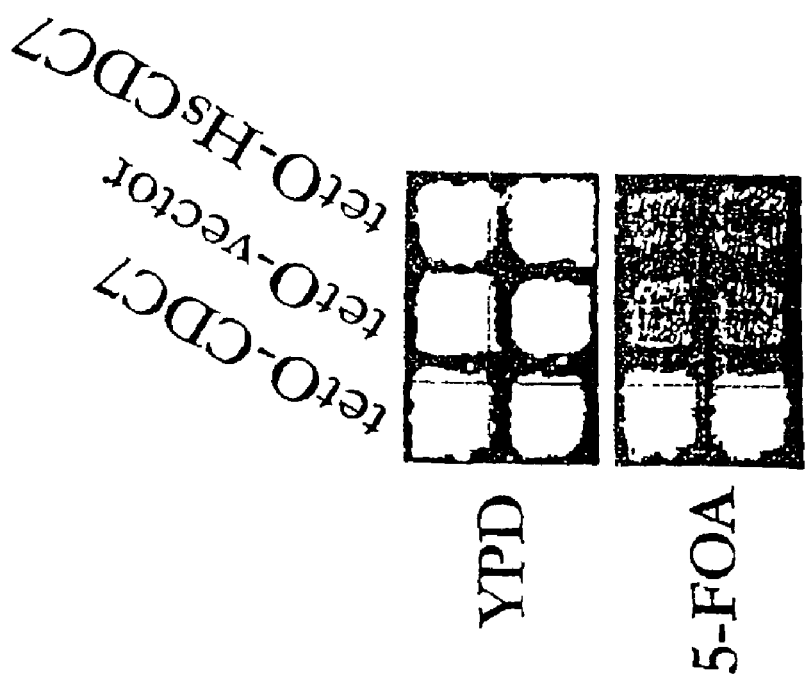
FIG. 4 is a representation of a complementation assay indicating that human HsCDC7 does not function in yeast.

Referring to FIG. 4, a plate growth assay demonstrated that tetO-HsCDC7 does not complement cdc7Δ. MMB2166 was transformed with p415-tetO-CDC7, p415-tetO, or p415-tetO-HsCDC7. Each open reading frame is under the control of a tetracycline responsive promoter. Two independent transformants were patched to non-selective media and then replica plated to plates containing 5-FOA. Only strains where the cdc7Δ mutation is complemented by the transformed plasmid grow, e.g., a plasmid expressing yeast CDC7 (first column, FIG. 4). Expression of HsCDC7 alone (under control of the tetO promoter) does not complement the cdc7Δ (third column, FIG. 4).

Figure 5:
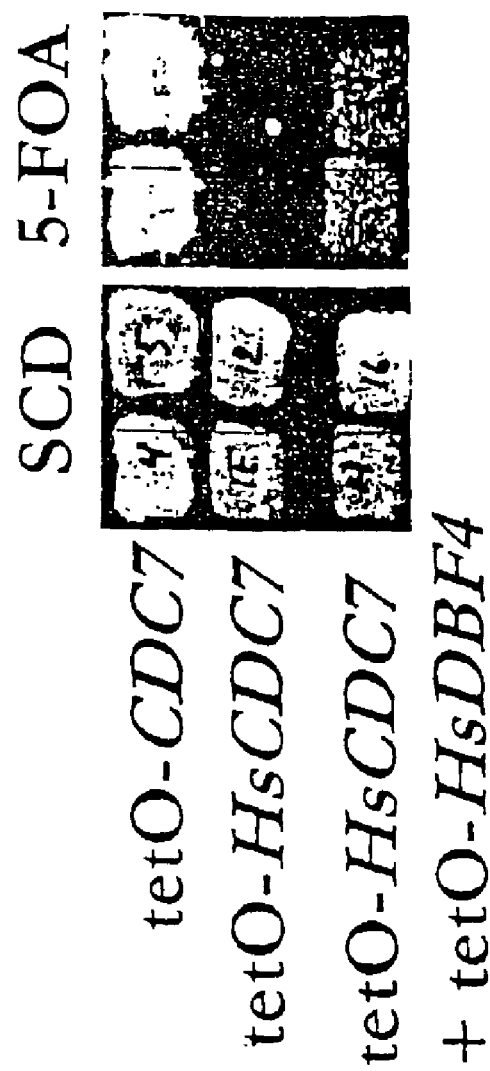
FIG. 5 is a representation of a complementation assay indicating that human HsCDC7 and human HsDBF4, in combination, function in yeast.

Referring to FIG. 5, a plate growth assay demonstrated that co-expression of HsCDC7 and HsDBF4 complements cdc7Δ. MMB2166 was transformed with p415-tetO-CDC7 independently, p411-HsCDC7 independently, and co-transformed with both p411-tetO-HsCDC7 and p415-tetO-HsDBF4. Two independent transformants of each of the three variations were tested for complementation of the cdc7Δ mutant phenotype. Only the strains transformed with nucleic acids encoding both HsCDC7 and HsDBF4 (or the yeast CDC7) are viable. This result indicates that both HsCDC7 and HsDBF4 are required to complement cdc7Δ.

Figure 6A:
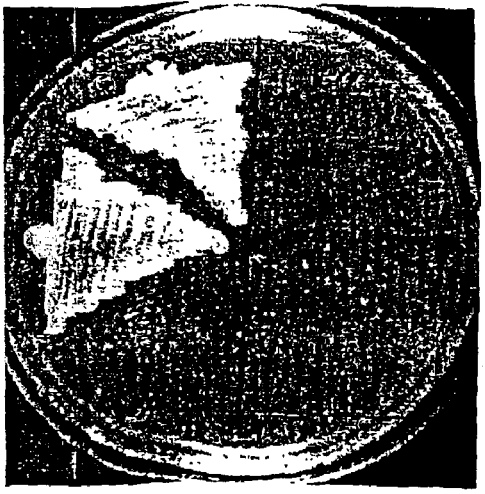
FIGS. 6A–C are representations of an assay indicating the requirement for the absence of doxycycline for tetO driven co-expression of human HsCDC7 and human HsDBF4 in yeast.
Figure 6B:
Figure 6C:
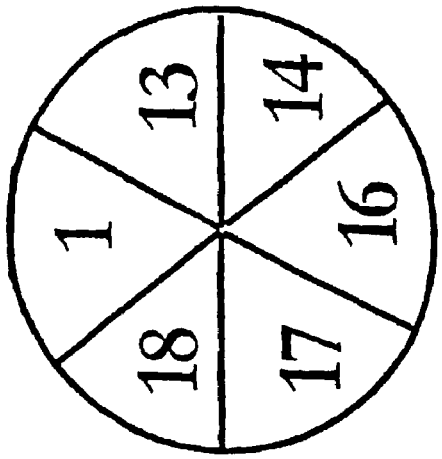

Referring to FIGS. 6A, 6B, and 6C, complementation of cdc7Δ by tetO driven co-expression of HsCdc7 and HsDbf4 is doxycycline sensitive. MMB2327 (#1), MMB2333 (#13) and multiple isolates of MMB2334 (#'s 14, 16, 17 and 18) were streaked onto Synthetic medium in the absence (FIG. 6A) or presence (FIG. 6B) of (5 μg/ml) doxycycline. Only strains with a copy of yeast CDC7 (under control of the CDC7 promoter) are able to grow in the presence of doxycycline.

Example 2

Construction of a Control bob1-1 Strain

Although CDC7 is an essential gene, a documented point mutation, bob1-1, is capable of completely bypassing CDC7 function. The allele bob1-1 is a mutant gene that has a single point mutation: P83L. The mutation bypasses the cell cycle arrest caused by loss of CDC7 function. The bob1-1 mutation was introduced into a yeast strain dependent on human CDC7 and DBF4.

Primers oBA255 and oBA258 were used to amplify a 0.63 kb PCR product that contained the first 270 bp of BOB1 along with 360 bp of the upstream promoter region. oBA258 contained a single G to A point mutation that produces a P83L single amino acid mutation. Primers oBA257 and oBA259 were used to generate a PCR product that amplified 570 bp downstream of the point mutation. These PCR products were subcloned into pRS303 at the XhoI-NotI sites. This plasmid was cut with SpeI and transformed into MMB2166. Transformants were selected on synthetic medium lacking histidine and scored for resistance to 5-fluoroorotic acid (5-FOA).

MMB2170 was crossed with MMB2326 to generate a heterozygous diploid at both the CDC7 and BOB1 loci. This diploid strain was sporulated, tetrads dissected and germinated spores were scored for the appropriate prototrophic markers and phenotypes. Crossing the appropriate haploid strains resulting from the previous cross generated diploids homozygous at both loci. Such diploid strains were co-transformed with p411-tetO-HsCDC7 and p415-tetO-HsDBF4 and strains that grew in the presence of 5-FOA were used. MMB2334 and MMB2491 were further confirmed by doxycycline (80 μg/ml) sensitive and resistant growth, respectively.

The resulting strain, MMB2491, an example of a control yeast strain, has the following genotype: cdc7Δ::KANsnq2Δ::HIS3 pdr5Δ::HIS3 bob1-1::HIS3+ p411-tetO:HsCDC7+p415-tetO:HsDSBF4.

The plasmids listed in Table I are exemplary nucleic acids and vector nucleic acids that can be used as described herein. Likewise, the yeast strains listed in Table II are exemplary yeast strains that can be used for the methods described herein. Table III lists oligonucleotides that can be used to construct the strains and nucleic acids described herein. Their sequences are also provided.

TABLE I

Plasmids

| Plasmid | Source | Markers, notes |
|---|---|---|
| pRS416 | ATCC, #87521 | CEN, URA3, amp |
| pRS416-CDC7 | Millennium Pharmaceuticals, Inc | CEN, URA3, amp |
| pRS411 | ATCC, #87521 | CEN, MET15, amp |
| p411-tetO | Millennium Pharmaceuticals, Inc | CEN, MET15, amp |
| p411-tetO-HsCDC7 | Millennium Pharmaceuticals, Inc | CEN, MET15, amp |
| pRS415 | ATCC, #87520 | CEN, LEU2, amp |
| p415-tetO | Millennium Pharmaceuticals, Inc | CEN, LEU2, amp |
| p415-tetO-CDC7 | Millennium Pharmaceuticals, Inc | CEN, LEU2, amp |

TABLE I-continued

Plasmids

| Plasmid | Source | Markers, notes |
|---|---|---|
| p415-tetO-HsCDC7 | Millennium Pharmaceuticals, Inc | CEN, LEU2, amp |
| p415-tetO-HsDBF4 | Millennium Pharmaceuticals, Inc | CEN, LEU2, amp |
| pRS303 | ATCC, #77138 | Int, HIS3, amp |
| pRS303-bob1-1 | Millennium Pharmaceuticals, Inc | Int, HIS3, amp |
| pFA6-kanMX4 | Wach, et al. (1994) Yeast 10:1793–1808 | PCR template for G418-selectable deletions |
| pCM188 | Gari, et al. (1997) Yeast 13:837–848 | CEN, URA3, tetO2 promoter, amp |

TABLE II

Yeast Strains

| Strain | Relevant genotype |
|---|---|
| BY4743* | MATa/α ura3 leu2 his3 met15/MET15 LYS2/lys2 |
| MMB1489 | MATa/α ura3 leu2 his3 MET15/met15 lys2/LYS2 snq2 pdr5 |
| MMB2166 | MATa cdc7 + pRS416-CDC7 |
| MMB2326 | MATα cdc7 + pRS416-CDC7 |
| MMB2327 | MATa cdc7 + pRS416-CDC7 + p-415-tetO-CDC7 |
| MMB2328 | MATa cdc7 + pRS416-CDC7 + p-411-tetO-HsCDC7 |
| MMB2333 | MATa/α cdc7 + pRS416-CDC7 + p-411-tetO-HsCDC7 + p415-tetO-HsDBF4 |
| MMB2334 | MATa/a cdc7 + p411-tetO-HsCDC7 + p415-tetO-HsDBF4 |
| MMB2170 | MATa cdc7 bob1-1 |
| MMB2491 | MATa/a cdc7 bob1-1 + p411-tetO-HsCDC7 + p415-tetO-HsDBF4 |

*ATCC, #201390, all other strains are from Millennium Pharmaceuticals, Inc.

TABLE III

Oligonucleotide primers

| Oligo # | Sequence (5'–3') | |
|---|---|---|
| oBA234 | GGAAAGAGGCAGTTTCGAAGTAGAACAATCATAATGACAAGCAA AACGCGTACGCTGCAGGTCGAC | (SEQ ID NO:1) |
| oBA235 | AGAACATCCTTATCGAGCAAATCTGCCTCGCTTGAGCTGACAACG ATCGATGAATTCGAGCTCG | (SEQ ID NO:2) |
| oBA236 | TGACCATGACAGTGTAGG | (SEQ ID NO:3) |
| oBA255 | GTCACTCGAGCCCTTTATTCTACCC | (SEQ ID NO:4) |
| oBA257 | GAAACTATCAGACGAACTTTCAGATATCATTCCATTATTCG | (SEQ ID NO:5) |
| oBA258 | CGAATAATGGAATGATATCTGAAAGTTCGTCTGATAGTTTC | (SEQ ID NO:6) |
| oBA259 | GTCAGCGGCCGCTACTGGAACCAGTTCTGGG | (SEQ ID NO:7) |
| oBA263 | GCGCGCGTAATACGACTCACTATAGGGCGAATTGGGTACCTGACC ATGACAGTGTAGG | (SEQ ID NO:8) |
| oBA264 | CGCTCTAGAACTAGTGGATCCCCCGGGCTGCAGGAATTCTAAGTA TCGTCTGCACCTGTGC | (SEQ ID NO:9) |

TABLE III-continued

Oligonucleotide primers

| Oligo # | Sequence (5'–3') | |
|---|---|---|
| oBA271 | TCATCCCAAGCTAGCGTAGTCAGGAACGTCATATGGATAGGCGCC GCTCATATCTTTAAAAAATGG | (SEQ ID NO:10) |
| oBA273 | CTAACCGTTGAGGTCTTCCTCACTGATCAATTTCTGTTCAGTAAAT GTAGAAGTTGAAGG | (SEQ ID NO:11) |
| oBA296 | CGTGAATGTAAGCGTGACATAACTAATTACATGATGCGGCCCTCCt caAGCGTAATCTGGAACGTC | (SEQ ID NO:12) |
| oBA297 | ACGCAAACACAAATACACACACTAAATTACCGGATCAATTCGGG GATGGAGGCGTCTTTGGGGATTC | (SEQ ID NO:13) |
| oBA298 | GCAGAAGAAGCTTTGTTGCATCCATTTTTTAAAGATATGAGCTTG ATCTTTTACCCATACGAT | (SEQ ID NO:14) |
| oBA299 | ACGCAAACACAAATACACACACTAAATTACCGGATCAATTCGGG GATGAACTCCGGAGCCATGAGG | (SEQ ID NO:15) |
| oBA300 | ACAGCGTTTTTCTCGTCCCCTTCAACTTCTACATTTACTGGCTTTCT CTGCGGCCGCTCTGAG | (SEQ ID NO:16) |
| oBA301 | CGTGAATGTAAGCGTGACATAACTAATTACATGATGCGGCCCTCC TCATCCACTAGTGCGGCCGCT | (SEQ ID NO:17) |

Example 3

Screening for Mammalian Cdc7 Inhibitors

The strain MMB2334, which has the following genotype: cdc7Δ::KAN snq2Δ::HIS3 pdr5Δ::HIS3+p411-tetO:HsCDC7+p415-tetO:HsDSBF4, is used as the yeast strain for the primary screen. A culture containing the strain is used to seed wells of a microtitre plate. Dilutions of test compounds from a chemical library are applied to each well in duplicate. Control wells are used to monitor the effects of buffer alone and other control solvents. After 24 hours of incubation at 30° C., the endogenous ATP levels of the cells in each well is measured. Wells that grew substantially slower as indicated by a lower level of endogenous ATP than the control wells are identified.

MMB2491, which has the following genotype: cdc7Δ::KAN snq2Δ::HIS3 pdr5Δ::HIS3 bob1-1::HIS3+ p411-tetO:HsCDC7+p415-tetO:HsDSBF4, is used for the secondary screen. Compounds that were identified in the primary screen are rescreened in the same format, except using a starter culture of yeast from MMB2491 strain. Compounds that do not inhibit the growth of this strain are identified. Such compounds are candidate inhibitors of human Cdc7·Dbf4.

OTHER EMBODIMENTS

A number of embodiments of the invention have been described. Nevertheless, it will be understood that various modifications may be made without departing from the spirit and scope of the invention. For example, any mammalian Cdc7 or Dbf4 can be used in place of human Cdc7 and Dbf4. Moreover, mutant, truncated and other modified forms of a mammalian Cdc7 and Dbf4 can be used so long as they are able to complement yeast Cdc7 activity and the yeast cdc7 mutant phenotype. Accordingly, other embodiments are within the scope of the following claims.

What is claimed:

1. A method for determining whether a test compound is an inhibitor of mammalian Cdc7·Dbf4 activity, the method comprising: (i) obtaining a yeast cell, the genetic complement of which comprises: a) an inactive allele of the yeast CDC7 gene; b) a first nucleic acid molecule that encodes a human Cdc7 polypeptide; and c) a second nucleic acid molecule that encodes a human Dbf4 polypeptide;
(ii) contacting the yeast cell with a test compound; and
(iii) assessing growth or cell cycle progression of the yeast cell, wherein a decrease in growth or cell cycle progression indicates that the test compound is an inhibitor of mammalian Cdc7·Dbf4 activity;
wherein the human Cdc7 polypeptide and the human Dbf4 polypeptide can genetically complement the inactive yeast CDC7 gene.

2. The method of claim 1, wherein assessing comprises culturing the yeast cell in a container.

3. The method of claim 2, wherein assessing comprises culturing the yeast cell on a solid medium within the container and monitoring the size of a colony formed by the yeast cell.

4. The method of claim 2, wherein assessing comprises culturing the yeast cell in a liquid medium within the container and determining the number of yeast cells in the liquid medium.

5. The method of claim 2, wherein assessing comprises culturing the yeast cell in a liquid medium within the container and measuring turbidity of the liquid medium.

6. The method of claim 1, wherein assessing comprises measuring endogenous ATP levels of the yeast cell.

7. The method of claim 1, wherein assessing comprises fluorescent-activated cell sorting based on DNA content.

8. The method of claim 1, further comprising assaying in vitro human Cdc7·Dbf4 kinase activity.

9. The method of claim 8, wherein assaying comprises determining human Cdc7·Dbf4 kinase activity for a minichromosome maintenance protein substrate.

* * * * *

SEQUENCE LISTING

<160> NUMBER OF SEQ ID NOS: 21

<210> SEQ ID NO 1
<211> LENGTH: 66
<212> TYPE: DNA
<213> ORGANISM: Artificial Sequence
<220> FEATURE:
<223> OTHER INFORMATION: Primer

<400> SEQUENCE: 1

```
ggaaagaggc agtttcgaag tagaacaatc ataatgacaa gcaaaacgcg tacgctgcag    60
gtcgac                                                              66
```

<210> SEQ ID NO 2
<211> LENGTH: 64

```
<212> TYPE: DNA
<213> ORGANISM: Artificial Sequence
<220> FEATURE:
<223> OTHER INFORMATION: Primer

<400> SEQUENCE: 2
agaacatcct tatcgagcaa atctgcctcg cttgagctga caacgatcga tgaattcgag    60
ctcg                                                                 64

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
tgaccatgac agtgtagg                                                  18

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
gtcactcgag ccctttattc taccc                                          25

<210> SEQ ID NO 5
<211> LENGTH: 41
<212> TYPE: DNA
<213> ORGANISM: Artificial Sequence
<220> FEATURE:
<223> OTHER INFORMATION: Primer

<400> SEQUENCE: 5
gaaactatca gacgaacttt cagatatcat tccattattc g                        41

<210> SEQ ID NO 6
<211> LENGTH: 41
<212> TYPE: DNA
<213> ORGANISM: Artificial Sequence
<220> FEATURE:
<223> OTHER INFORMATION: Primer

<400> SEQUENCE: 6
cgaataatgg aatgatatct gaaagttcgt ctgatagttt c                        41

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gtcagcggcc gctactggaa ccagttctgg g                                   31

<210> SEQ ID NO 8
<211> LENGTH: 58
<212> TYPE: DNA
<213> ORGANISM: Artificial Sequence
<220> FEATURE:
<223> OTHER INFORMATION: Primer
```

-continued

```
<400> SEQUENCE: 8
gcgcgcgtaa tacgactcac tatagggcga attgggtacc tgaccatgac agtgtagg        58

<210> SEQ ID NO 9
<211> LENGTH: 61
<212> TYPE: DNA
<213> ORGANISM: Artificial Sequence
<220> FEATURE:
<223> OTHER INFORMATION: Primer

<400> SEQUENCE: 9
cgctctagaa ctagtggatc ccccgggctg caggaattct aagtatcgtc tgcacctgtg        60
c                                                                       61

<210> SEQ ID NO 10
<211> LENGTH: 66
<212> TYPE: DNA
<213> ORGANISM: Artificial Sequence
<220> FEATURE:
<223> OTHER INFORMATION: Primer

<400> SEQUENCE: 10
tcatcccaag ctagcgtagt caggaacgtc atatggatag gcgccgctca tatctttaaa        60
aaatgg                                                                  66

<210> SEQ ID NO 11
<211> LENGTH: 60
<212> TYPE: DNA
<213> ORGANISM: Artificial Sequence
<220> FEATURE:
<223> OTHER INFORMATION: Primer

<400> SEQUENCE: 11
ctaaccgttg aggtcttcct cactgatcaa tttctgttca gtaaatgtag aagttgaagg        60

<210> SEQ ID NO 12
<211> LENGTH: 66
<212> TYPE: DNA
<213> ORGANISM: Artificial Sequence
<220> FEATURE:
<223> OTHER INFORMATION: Primer

<400> SEQUENCE: 12
cgtgaatgta agcgtgacat aactaattac atgatgcggc cctcctcaag cgtaatctgg        60
aacgtc                                                                  66

<210> SEQ ID NO 13
<211> LENGTH: 67
<212> TYPE: DNA
<213> ORGANISM: Artificial Sequence
<220> FEATURE:
<223> OTHER INFORMATION: Primer

<400> SEQUENCE: 13
acgcaaacac aaatacacac actaaattac cggatcaatt cggggatgga ggcgtctttg        60
gggattc                                                                 67

<210> SEQ ID NO 14
<211> LENGTH: 63
<212> TYPE: DNA
<213> ORGANISM: Artificial Sequence
<220> FEATURE:
<223> OTHER INFORMATION: Primer
```

```
<400> SEQUENCE: 14
gcagaagaag ctttgttgca tccatttttt aaagatatga gcttgatctt ttacccatac      60
gat                                                                   63

<210> SEQ ID NO 15
<211> LENGTH: 66
<212> TYPE: DNA
<213> ORGANISM: Artificial Sequence
<220> FEATURE:
<223> OTHER INFORMATION: Primer

<400> SEQUENCE: 15
acgcaaacac aaatacacac actaaattac cggatcaatt cggggatgaa ctccggagcc      60
atgagg                                                                66

<210> SEQ ID NO 16
<211> LENGTH: 63
<212> TYPE: DNA
<213> ORGANISM: Artificial Sequence
<220> FEATURE:
<223> OTHER INFORMATION: Primer

<400> SEQUENCE: 16
acagcgtttt tctcgtcccc ttcaacttct acatttactg gctttctctg cggccgctct      60
gag                                                                   63

<210> SEQ ID NO 17
<211> LENGTH: 66
<212> TYPE: DNA
<213> ORGANISM: Artificial Sequence
<220> FEATURE:
<223> OTHER INFORMATION: Primer

<400> SEQUENCE: 17
cgtgaatgta agcgtgacat aactaattac atgatgcggc cctcctcatc cactagtgcg      60
gccgct                                                                66

<210> SEQ ID NO 18
<211> LENGTH: 1725
<212> TYPE: DNA
<213> ORGANISM: Homo sapiens

<400> SEQUENCE: 18
atggaggcgt ctttggggat tcagatggat gagccaatgg cttttctctcc ccagcgtgac      60 cggtttcagg ctgaaggctc tttaaaaaaa aacgagcaga ttttaaaact tgcaggtgtt     120
aaaaaagata ttgagaagct ttatgaagct gtaccacagc ttagtaatgt gtttaagatt     180
gaggacaaaa ttggagaagg cactttcagc tctgtttatt tggccacagc acagttacaa     240
gtaggacctg aagagaaaat tgctctaaaa cacttgattc aacaagtcca tcctataaga     300
attgcagctg aacttcagtg cctaacagtg gctggggggc aagataatgt catgggagtt     360
aaatactgct ttaggaagaa tgatcatgta gttattgcta tgccatatct ggagcatgag     420 tcgttttttgg acattctgaa ttctctttcc tttcaagaag tacgggaata tatgcttaat     480
ctgttcaaag ctttgaaacg cattcatcag tttggtattg ttcaccgtga tgttaagccc     540
agcaattttt tatataatag gcgcctgaaa agtatgcct tggtagactt tggtttggcc     600
caaggaaccc atgatacgaa aatagagctt cttaaatttg tccagtctga agctcagcag     660
```

-continued

```
gaaaggtgtt cacaaaacaa atcccacata atcacaggaa acaagattcc actgagtggc    720
ccagtaccta aggagctgga tcagcagtcc accacaaaag cttctgttaa agaccctac     780 acaaatgcac aaattcagat taaacaagga aaagacggaa aggagggatc tgtaggcctt    840
tctgtccagc gctctgtttt tggagaaaga aatttcaata tacacagctc catttcacat    900
gagagccctg cagtgaaact catgaagcag tcaaagactg tggatgtact gtctagaaag    960
ttagcaacaa aaagaaggc tatttctacg aaagttatga atagtgctgt gatgaggaaa    1020
actgccagtt cttgcccagc tagcctgacc tgtgactgct atgcaacaga taaagtttgt    1080
agtatttgcc tttcaaggcg tcagcaggtt gcccctaggg caggtacacc aggattcaga    1140
gcaccagagg tcttgacaaa gtgccccaat caaactacag caattgacat gtggtctgca    1200
ggtgtcatat ttctttcttt gcttagtgga cgatatccat tttataaagc aagtgatgat    1260
ttaactgctt tggcccaaat tatgacaatt aggggatcca gagaaactat ccaagctgct    1320 aaaactttg ggaaatcaat attatgtagc aagaagttc cagcacaaga cttgagaaaa     1380
ctctgtgaga gactcagggg tatggattct agcactccca agttaacaag tgatatacaa    1440
gggcatgctt ctcatcaacc agctatttca gagaagactg accataaagc ttcttgcctc    1500
gttcaaacac ctccaggaca atactcaggg aattcattta aaaggggga tagtaatagc    1560 tgtgagcatt gttttgatga gtataatacc aatttagaag ctggaatgaa ggtacctgat    1620
gaagcttatg acctgcttga taaacttcta gatctaaatc cagcttcaag aataacagca    1680
gaagaagctt tgttgcatcc atttttaaa gatatgagct gtga                    1725
```

<210> SEQ ID NO 19
<211> LENGTH: 574
<212> TYPE: PRT
<213> ORGANISM: Homo sapiens

<400> SEQUENCE: 19

```
Met Glu Ala Ser Leu Gly Ile Gln Met Asp Glu Pro Met Ala Phe Ser
1               5                   10                  15

Pro Gln Arg Asp Arg Phe Gln Ala Glu Gly Ser Leu Lys Lys Asn Glu
            20                  25                  30

Gln Asn Phe Lys Leu Ala Gly Val Lys Lys Asp Ile Glu Lys Leu Tyr
        35                  40                  45

Glu Ala Val Pro Gln Leu Ser Asn Val Phe Lys Ile Glu Asp Lys Ile
    50                  55                  60

Gly Glu Gly Thr Phe Ser Ser Val Tyr Leu Ala Thr Ala Gln Leu Gln
65                  70                  75                  80

Val Gly Pro Glu Glu Lys Ile Ala Leu Lys His Leu Ile Pro Thr Ser
                85                  90                  95

His Pro Ile Arg Ile Ala Ala Glu Leu Gln Cys Leu Thr Val Ala Gly
            100                 105                 110

Gly Gln Asp Asn Val Met Gly Val Lys Tyr Cys Phe Arg Lys Asn Asp
        115                 120                 125

His Val Val Ile Ala Met Pro Tyr Leu Glu His Glu Ser Phe Leu Asp
    130                 135                 140

Ile Leu Asn Ser Leu Ser Phe Gln Glu Val Arg Glu Tyr Met Leu Asn
145                 150                 155                 160

Leu Phe Lys Ala Leu Lys Arg Ile His Gln Phe Gly Ile Val His Arg
                165                 170                 175

Asp Val Lys Pro Ser Asn Phe Leu Tyr Asn Arg Arg Leu Lys Lys Tyr
            180                 185                 190
```

Ala Leu Val Asp Phe Gly Leu Ala Gln Gly Thr His Asp Thr Lys Ile
            195                 200                 205

Glu Leu Leu Lys Phe Val Gln Ser Glu Ala Gln Gln Glu Arg Cys Ser
        210                 215                 220

Gln Asn Lys Ser His Ile Ile Thr Gly Asn Lys Ile Pro Leu Ser Gly
225                 230                 235                 240

Pro Val Pro Lys Glu Leu Asp Gln Gln Ser Thr Thr Lys Ala Ser Val
            245                 250                 255

Lys Arg Pro Tyr Thr Asn Ala Gln Ile Gln Ile Lys Gln Gly Lys Asp
        260                 265                 270

Gly Lys Glu Gly Ser Val Gly Leu Ser Val Gln Arg Ser Val Phe Gly
        275                 280                 285

Glu Arg Asn Phe Asn Ile His Ser Ser Ile Ser His Glu Ser Pro Ala
        290                 295                 300

Val Lys Leu Met Lys Gln Ser Lys Thr Val Asp Val Leu Ser Arg Lys
305                 310                 315                 320

Leu Ala Thr Lys Lys Ala Ile Ser Thr Lys Val Met Asn Ser Ala
        325                 330                 335

Val Met Arg Lys Thr Ala Ser Ser Cys Pro Ala Ser Leu Thr Cys Asp
        340                 345                 350

Cys Tyr Ala Thr Asp Lys Val Cys Ser Ile Cys Leu Ser Arg Arg Gln
        355                 360                 365

Gln Val Ala Pro Arg Ala Gly Thr Pro Gly Phe Arg Ala Pro Glu Val
        370                 375                 380

Leu Thr Lys Cys Pro Asn Gln Thr Thr Ala Ile Asp Met Trp Ser Ala
385                 390                 395                 400

Gly Val Ile Phe Leu Ser Leu Leu Ser Gly Arg Tyr Pro Phe Tyr Lys
            405                 410                 415

Ala Ser Asp Asp Leu Thr Ala Leu Ala Gln Ile Met Thr Ile Arg Gly
        420                 425                 430

Ser Arg Glu Thr Ile Gln Ala Ala Lys Thr Phe Gly Lys Ser Ile Leu
        435                 440                 445

Cys Ser Lys Glu Val Pro Ala Gln Asp Leu Arg Lys Leu Cys Glu Arg
450                 455                 460

Leu Arg Gly Met Asp Ser Ser Thr Pro Lys Leu Thr Ser Asp Ile Gln
465                 470                 475                 480

Gly His Ala Ser His Gln Pro Ala Ile Ser Glu Lys Thr Asp His Lys
            485                 490                 495

Ala Ser Cys Leu Val Gln Thr Pro Pro Gly Gln Tyr Ser Gly Asn Ser
        500                 505                 510

Phe Lys Lys Gly Asp Ser Asn Ser Cys Glu His Cys Phe Asp Glu Tyr
        515                 520                 525

Asn Thr Asn Leu Glu Gly Trp Asn Glu Val Pro Asp Glu Ala Tyr Asp
        530                 535                 540

Leu Leu Asp Lys Leu Leu Asp Leu Asn Pro Ala Ser Arg Ile Thr Ala
545                 550                 555                 560

Glu Glu Ala Leu Leu His Pro Phe Phe Lys Asp Met Ser Leu
            565                 570

<210> SEQ ID NO 20
<211> LENGTH: 2025
<212> TYPE: DNA
<213> ORGANISM: Homo sapiens -continued

```
<400> SEQUENCE: 20
atgaactccg gagccatgag gatccacagt aaaggacatt tccagggtgg aatccaagtc      60
aaaaatgaaa aaaacagacc atctctgaaa tctctgaaaa ctgataacag gccagaaaaa     120
tccaaatgta agccactttg gggaaaagta ttttaccttg acttaccttc tgtcaccata     180
tctgaaaaac ttcaaaagga cattaaggat ctgggagggc gagttgaaga atttctcagc     240
aaagatatca gttatcttat ttcaaataag aaggaagcta aatttgcaca aaccttgggt     300
cgaatttctc ctgtaccaag tccagaatct gcatatactg cagaaaccac ttcacctcat     360
cccagccatg atggaagttc atttaagtca ccagacacag tgtgtttaag cagaggaaaa     420
ttattagttg aaaaagctat caaggaccat gattttattc cttcaaatag tatattatca     480
aatgccttgt catggggagt aaaaattctt catattgatg acattagata ctacattgaa     540
caaaagaaaa aagagttgta tttactcaag aaatcaagta cttcagtaag agatgggggc     600
aaaagagttg gtagtggtgc acaaaaaaca gaacaggaa gactcaaaaa gccttttgta      660
aaggtggaag atatgagcca actttatagg ccattttatc ttcagctgac caatatgcct     720
tttataaatt attctattca gaagccctgc agtccatttg atgtagacaa gccatctagt     780
atgcaaaagc aaactcaggt taaactaaga atccaaacag atggcgataa gtatggtgga     840
acctcaattc aactccagtt gaaagagaag aagaaaaaag gatattgtga atgttgcttg     900
cagaaatatg aagatctaga aactcacctt ctaagtgagc aacacagaaa ctttgcacag     960
agtaaccagt atcaagttgt tgatgatatt gtatctaagt tagttttga ctttgtggaa     1020 tatgaaaagg acacacctaa aaagaaaaga ataaaataca gtgttggatc cctttctcct    1080
gtttctgcaa gtgtcctgaa aaagactgaa caaaaggaaa aagtggaatt gcaacatatt    1140
tctcagaaag attgccagga agatgataca acagtgaagg agcagaattt cctgtataaa    1200
gagacccagg aaactgaaaa aaagctcctg tttatttcag agcccatccc ccaccccttca   1260 aatgaattga gagggcttaa tgagaaaatg agtaataaat gttccatgtt aagtacagct    1320
gaagatgaca taagacagaa ttttacacag ctacctctac ataaaaacaa acaggaatgc    1380
attcttgaca tttccgaaca cacattaagt gaaaatgact tagaagaact aagggtagat    1440
cactataaat gtaacataca ggcatctgta catgtttctg atttcagtac agataatagt    1500
ggatctcaac caaaacagaa gtcagatact gtgcttttc cagcaaagga tctcaaggaa     1560
aaggaccttc attcaatatt tactcatgat tctggtctga taacaataaa cagttcacaa    1620
gagcacctaa ctgttcaggc aaaggctcca ttccatactc ctcctgagga acccaatgaa    1680
tgtgacttca agaatatgga tagtttacct tctggtaaaa tacatcgaaa agtgaaaata    1740
atattaggac gaaatagaaa agaaaatctg gaaccaaatg ctgaatttga taaagaact     1800 gaatttatta cacaagaaga aaacagaatt tgtagttcac cggtacagtc tttactagac    1860
ttgtttcaga ctagtgaaga gaaatcagaa ttttgggtt tcacaagcta cacagaaaag    1920
agtggtatat gcaatgtttt agatatttgg gaagaggaaa attcagataa tctgttaaca    1980
gcgtttttct cgtccccttc aacttctaca tttactggct tttag                    2025
```

<210> SEQ ID NO 21
<211> LENGTH: 674
<212> TYPE: PRT
<213> ORGANISM: Homo sapiens

<400> SEQUENCE: 21

Met Asn Ser Gly Ala Met Arg Ile His Ser Lys Gly His Phe Gln Gly

-continued

```
  1               5                   10                  15
Gly Ile Gln Val Lys Asn Glu Lys Asn Arg Pro Ser Leu Lys Ser Leu
                 20                  25                  30
Lys Thr Asp Asn Arg Pro Glu Lys Ser Lys Cys Lys Pro Leu Trp Gly
                 35                  40                  45
Lys Val Phe Tyr Leu Asp Leu Pro Ser Val Thr Ile Ser Glu Lys Leu
                 50                  55                  60
Gln Lys Asp Ile Lys Asp Leu Gly Gly Arg Val Glu Glu Phe Leu Ser
 65                  70                  75                  80
Lys Asp Ile Ser Tyr Leu Ile Ser Asn Lys Lys Glu Ala Lys Phe Ala
                 85                  90                  95
Gln Thr Leu Gly Arg Ile Ser Pro Val Pro Ser Pro Glu Ser Ala Tyr
                100                 105                 110
Thr Ala Glu Thr Thr Ser Pro His Pro Ser His Asp Gly Ser Ser Phe
                115                 120                 125
Lys Ser Pro Asp Thr Val Cys Leu Ser Arg Gly Lys Leu Leu Val Glu
130                 135                 140
Lys Ala Ile Lys Asp His Asp Phe Ile Pro Ser Asn Ser Ile Leu Ser
145                 150                 155                 160
Asn Ala Leu Ser Trp Gly Val Lys Ile Leu His Ile Asp Asp Ile Arg
                165                 170                 175
Tyr Tyr Ile Glu Gln Lys Lys Glu Leu Tyr Leu Leu Lys Lys Ser
                180                 185                 190
Ser Thr Ser Val Arg Asp Gly Lys Arg Val Gly Ser Gly Ala Gln
                195                 200                 205
Lys Thr Arg Thr Gly Arg Leu Lys Lys Pro Phe Val Lys Val Glu Asp
                210                 215                 220
Met Ser Gln Leu Tyr Arg Pro Phe Tyr Leu Gln Leu Thr Asn Met Pro
225                 230                 235                 240
Phe Ile Asn Tyr Ser Ile Gln Lys Pro Cys Ser Pro Phe Asp Val Asp
                245                 250                 255
Lys Pro Ser Ser Met Gln Lys Gln Thr Gln Val Lys Leu Arg Ile Gln
                260                 265                 270
Thr Asp Gly Asp Lys Tyr Gly Gly Thr Ser Ile Gln Leu Gln Leu Lys
                275                 280                 285
Glu Lys Lys Lys Gly Tyr Cys Glu Cys Leu Gln Lys Tyr Glu
                290                 295                 300
Asp Leu Glu Thr His Leu Leu Ser Glu Gln His Arg Asn Phe Ala Gln
305                 310                 315                 320
Ser Asn Gln Tyr Gln Val Val Asp Asp Ile Val Ser Lys Leu Val Phe
                325                 330                 335
Asp Phe Val Glu Tyr Glu Lys Asp Thr Pro Lys Lys Arg Ile Lys
                340                 345                 350
Tyr Ser Val Gly Ser Leu Ser Pro Val Ser Ala Ser Val Leu Lys Lys
                355                 360                 365
Thr Glu Gln Lys Glu Lys Val Glu Leu Gln His Ile Ser Gln Lys Asp
                370                 375                 380
Cys Gln Glu Asp Asp Thr Thr Val Lys Glu Gln Asn Phe Leu Tyr Lys
385                 390                 395                 400
Glu Thr Gln Glu Thr Glu Lys Lys Leu Leu Phe Ile Ser Glu Pro Ile
                405                 410                 415
Pro His Pro Ser Asn Glu Leu Arg Gly Leu Asn Glu Lys Met Ser Asn
                420                 425                 430
```

-continued

```
Lys Cys Ser Met Leu Ser Thr Ala Glu Asp Asp Ile Arg Gln Asn Phe
        435                 440                 445

Thr Gln Leu Pro Leu His Lys Asn Lys Gln Glu Cys Ile Leu Asp Ile
        450                 455                 460

Ser Glu His Thr Leu Ser Glu Asn Asp Leu Glu Glu Leu Arg Val Asp
465                     470                 475                 480

His Tyr Lys Cys Asn Ile Gln Ala Ser Val His Val Ser Asp Phe Ser
                485                 490                 495

Thr Asp Asn Ser Gly Ser Gln Pro Lys Gln Lys Ser Asp Thr Val Leu
            500                 505                 510

Phe Pro Ala Lys Asp Leu Lys Glu Lys Asp Leu His Ser Ile Phe Thr
        515                 520                 525

His Asp Ser Gly Leu Ile Thr Ile Asn Ser Ser Gln Glu His Leu Thr
    530                 535                 540

Val Gln Ala Lys Ala Pro Phe His Thr Pro Pro Glu Glu Pro Asn Glu
545                 550                 555                 560

Cys Asp Phe Lys Asn Met Asp Ser Leu Pro Ser Gly Lys Ile His Arg
                565                 570                 575

Lys Val Lys Ile Ile Leu Gly Arg Asn Arg Lys Glu Asn Leu Glu Pro
            580                 585                 590

Asn Ala Glu Phe Asp Lys Arg Thr Glu Phe Ile Thr Gln Glu Glu Asn
        595                 600                 605

Arg Ile Cys Ser Ser Pro Val Gln Ser Leu Leu Asp Leu Phe Gln Thr
    610                 615                 620

Ser Glu Glu Lys Ser Glu Phe Leu Gly Phe Thr Ser Tyr Thr Glu Lys
625                 630                 635                 640

Ser Gly Ile Cys Asn Val Leu Asp Ile Trp Glu Glu Glu Asn Ser Asp
                645                 650                 655

Asn Leu Leu Thr Ala Phe Phe Ser Ser Pro Ser Thr Ser Thr Phe Thr
            660                 665                 670

Gly Phe
```